United States Patent [19]

Suzuki et al.

[11] Patent Number: 4,956,287
[45] Date of Patent: Sep. 11, 1990

[54] PROCESS FOR PRODUCING OLEAGINOUS COMPOSITION

[75] Inventors: Kazuaki Suzuki; Shoji Maruzeni; Eiji Nakai; Toru Nezu, all of Tokyo, Japan

[73] Assignee: Asahi Denka Kogyo Kabushiki Kaisha, Tokyo, Japan

[21] Appl. No.: 132,213

[22] Filed: Dec. 14, 1987

[30] Foreign Application Priority Data

Dec. 23, 1986 [JP] Japan ................................ 61-307358
Nov. 9, 1987 [JP] Japan ................................ 62-282646

[51] Int. Cl.$^5$ .......................... C12N 9/20; C12P 7/64; C07H 13/02; C07H 1/00
[52] U.S. Cl. .................................... 435/134; 435/198; 536/119; 536/124; 536/103; 536/110; 536/112; 536/58; 536/63
[58] Field of Search ............................. 435/134, 198; 260/410.7; 536/119, 124, 103, 110, 112, 58, 63

[56] References Cited

U.S. PATENT DOCUMENTS

Re. 28,729  3/1976  Yetter ................................ 426/607
4,705,692  11/1987  Tanaka et al. ...................... 426/607
4,874,699  10/1989  Maruzeni et al. ................... 435/135

Primary Examiner—Ronald W. Griffin
Assistant Examiner—Pamela S. Webber
Attorney, Agent, or Firm—Frishauf, Holtz, Goodman & Woodward

[57] ABSTRACT

The process for producing an oleaginous composition of the present invention comprises transesterifying a fat containing a large amount of polybasic unsaturated fatty acid(s) as constituting fatty acid(s) with saturated fatty acid(s) and/or saturated fatty acid alcohol ester(s) with the use of a lipase having an site-specificity to thereby give symmetric triglyceride(s) wherein the fatty acid groups at the 1- and 3-positions are selectively transesterified and a polybasic unsaturated fatty acid group is present at the 2-position. The above transesterification should be carried out under such conditions as to give an oleaginous composition which comprises 40% or more of symmetric triglyceride(s) each having a polybasic unsaturated fatty acid group at the 2-position and 50% or more of completely saturated fatty acid(s) each having 16 or more carbon atoms.

11 Claims, 1 Drawing Sheet

PROCESS FOR PRODUCING OLEAGINOUS COMPOSITION

BACKGROUND OF THE INVENTION

1. Field of the Invention

This invention relates to a process for producing an oleaginous composition. More particularly, it relates to a process for producing an oleaginous composition which has a high nutritive value, shows excellent melting behaviors and is highly available as a confectionery fat such as a hard butter.

2. Description of the Prior Art

Conventional hard butters mainly comprise symmetric triglycerides including oleodipalmitin (POP), oleopalmitostearin (SOP) and oledistearin (SOS), each having an oleate group at the 2-position, similar to cacao fat.

In order to further elevate the nutritive value of a confectionery fat such as a hard butter, it is necessary to introduce more nutritious polybasic unsaturated fatty acids such as linolic, linolenic, arachidonic, eicosapentaenoic and docosahexaenoic acids thereto.

It is expected that these polybasic unsaturated fatty acids, which are essential fatty acids and serve each as a precursor of a hormone-like substance such as prostaglandin, leukotriene and thromboxane, may exert some pharmacological effects, for example, improving arteriosclerosis and lowering the blood cholesterol level.

In order to introduce highly nutritious linoleic acid into a hard butter, a liquid oil containing a large amount of linolic acid may be blended with the hard butter. However it was reported that a hard butter comprising a liquid oil containing a large amount of linoleic acid, i.e., corn oil would exhibit an insufficient hardness and that the presence of a symmetric triglyceride (SLS) having an linolate group at the 2-position in a symmetric triglyceride would deteriorate the physical properties of the hard butter even at a content as low as 5% (cf. Japanese Patent Publication No. 28530/1982).

Further it was reported that when the content of linoleic acid in an oily material exceeded 14%, the resulting confectionery fat showed undersirable physical properties (cf. Japanese Patent Laid-Open No. 155048/1987).

Thus it has been believed hitherto that the presence of polybasic unsaturated fatty acids such as linoleic acid in a confectionery fat is undesirable.

OBJECTS AND SUMMARY OF THE INVENTION

It is an object of the present invention to provide a process for producing an oleaginous composition comprising a large amount of triglyceride(s) each having a polybasic unsaturated fatty acid group at the 2-position, which has a high nutritive value, shows excellent melting behaviors and is highly available as a confectionery fat.

The above object of the present invention has been achieved by providing a process for producing an oleaginous composition which comprises transesterifying a fat comprising a large amount of polybasic unsaturated fatty acid group(s) as the constituting fatty acid group(s) with saturated fatty acid(s) and/or saturated fatty acid alcohol ester(s) with the use of a lipase having a site-specificity to thereby give an oleaginous composition which comprises 40% or more of symmetric triglyceride(s) each having a polybasic unsaturated fatty acid group at the 2-position and 50% or more of completely saturated fatty acid(s) each having 16 or more carbon atoms.

According to the process for producing an oleaginous composition of the present invention, an oleaginous composition comprising a large amount of symmetric triglyceride(s) each having a polybasic unsaturated fatty acid group at the 2-position, which has a high nutritive value, shows excellent melting behaviors and is highly available as a confectionery fat, can be efficiently produced by transesterifying a fat comprising a large amount of polybasic unsaturated fatty acid groups as constituting fatty acid groups with the use of a lipase.

DETAILED DESCRIPTION OF THE INVENTION

Figure 1:
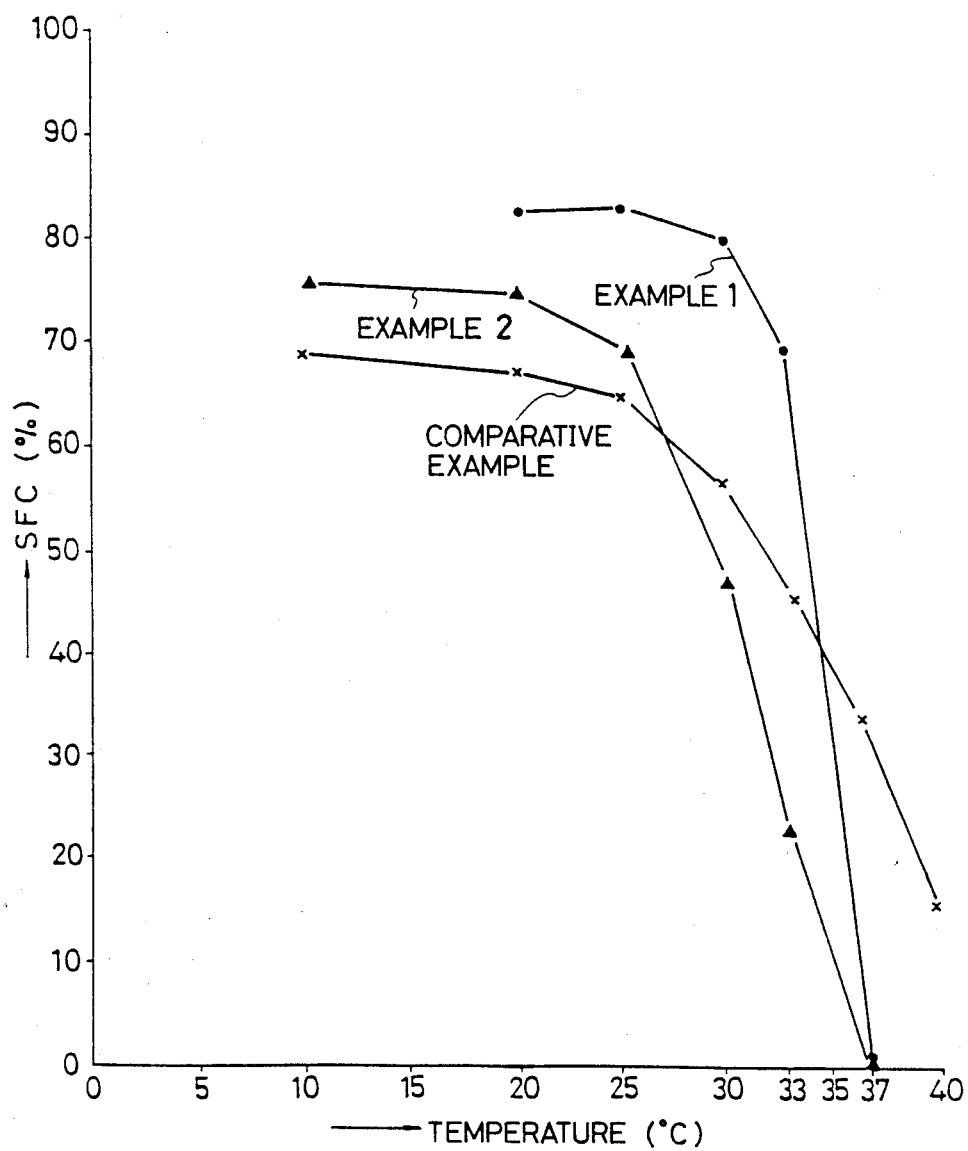
FIG. 1 is a graph showing the SFC curves of the oleaginous compositions obtained in Examples 1 and 2, each according to the present invention, and that obtained in Comparative Example.

Examples of the fat containing a large amount of polybasic unsaturated fatty acid(s) to be used in the present invention include those containing polybasic unsaturated fatty acids such as linoleic or linolenic acid as constituting fatty acids, for example, corn oil, soybean oil, rice bran oil, evening primrose oil, linseed oil, fish oil, safflower oil and sunflower oil, each optionally hydrogenated, as well as mixtures thereof.

Preferably examples of the saturated fatty acids to be used in the present invention include those having 16 to 18 carbon atoms, such as palmitic and stearic acids. Alcohol esters of these fatty acids are also available. Further saturated fatty acids such as arachic or behenic acid may be employed therefor. Examples of the saturated fatty acid alcohol esters to be used in the present invention include those obtained by esterifying one of the abovementioned saturated fatty acids with a straight-chain saturated monohydric alcohol having one to six carbon atoms, for example, methyl palmitate, ethyl palmitate, methyl stearate and ethyl stearate.

The lipase having a site-specificity to be used in the present invention should exert its effect exclusively on the fatty acids at the 1- and 3-positions of a triglyceride. Examples thereof include those originating from the genera Rhizopus and Aspergillus.

Thus according to the process of the present invention, said fat containing polyvalent unsaturated fatty acid(s) and said saturated fatty acid(s) and/or said saturated fatty acid alcohol ester(s) are transesterified with the use of said lipase to thereby selectively transesterify the fatty acid groups at the 1- and 3-positions of the fat containing the polybasic unsaturated fatty acid groups. Thus symmetric triglyceride(s) each having a polybasic unsaturated fatty acid group at the 2-position can be obtained.

The transesterification as describe above may be carried out in a conventional manner, for example, the one described in Japanese Patent Publication No. 43678/1987. The transesterification should be controlled in such a manner as to give the oleaginous composition of the present invention which comprises 40% or more of symmetric triglyceride(s) each having a polybasic unsaturated fatty acid group at the 2-position and 50% or more of completely saturated fatty acid(s) each having 16 or more carbon atoms.

When the content of the symmetric triglyceride(s) each having a polybasic unsaturated fatty acid group at the 2-position is less than 40% or the content of the completely saturated fatty acids each having 16 or more carbon atoms is less than 50%, an oleaginous composition having desirable properties as a confectionery fat, for example, an excellent meltability in mouth, little separation of liquid oil and solid fat and a steep solid fat content (SFC) curve can not be obtained.

After the completion of the transesterification, the employed enzyme and carrier are removed from the reaction mixture. Then the reaction mixture is subjected to post treatment(s) such as purification or fractionation, if required. Thus the aimed oleaginous composition of the present invention can be efficiently obtained.

To further illustrate the present invention, the following Examples and Comparative Example will be given.

EXAMPLE 1

300 g of corn salad oil, 360 g of stearic acid, 500 g of technical-grade hexane and 0.9 g (100,000 U/g) of watery Rhizopus delemar were treated at 40° C. for 24 hours to effect transesterification. After the completion of the reaction, the hexane was distilled off and the residue was treated on a silica gel column to thereby give a triglyceride (TG) fraction. The obtained triglycerides were further fractionated with the use of a solvent. Thus an oleaginous composition of the present invention was obtained as a crystalline fraction. Table 1 shows the analytical data of this oleaginous composition. The solid fat content (SFC) was determined by pulse NMR. Fatty acid groups at the 2-positions of the triglycerides were analyzed with the use of a lipase. FIG. 1 shows the SFC curve of the abovementioned oleaginous composition.

EXAMPLE 2

3000 g of linseed oil, 300 g of stearic acid, 500 g of technical-grade hexane and 0.9 g (100,000 U/g) of watery Rhizopus delemar were treated in the same manner as the one described in Example 1. The TG fraction thus obtained was further fractionated with a solvent to give an oleaginous composition of the present invention as a crystalline fraction. Table 1 shows the analytical data of this oleaginous composition. The solid fat content (SFC) was determined by pulse NMR. Fatty acid groups at the 2-positions of the triglycerides were analyzed with the use of a lipase. FIG. 1 shows the SFC curve of the abovementioned oleaginous composition.

COMPARATIVE EXAMPLE

35% of corn salad oil was blended with kokum fat having an abundance of SOS to give an oleaginous composition. Table 1 shows the analytical data of this oleaginous composition, while FIG. 1 shows the SFC curve thereof.

The results as shown in Table 1 indicate the following facts.

The oleaginous composition as prepared in Example 1, which contained a slightly larger amount of linolic acid than the one prepared in Comparative Example did, had a high solid fat content and was hard at room temperature but showed a solid fat content of almost 0% around the bodily temperature, thus giving a high meltability in mouth. The oleaginous composition as prepared in Example 2, which contained a large amount of linolenic acid, had a high solid fat content and was hard at room temperature but showed a solid fat content of 0% around the bodily temperature, thus giving a high meltability in mouth.

TABLE 1

|  | Ex. 1 | | Ex. 2 | | Comp. Ex. | |
| --- | --- | --- | --- | --- | --- | --- |
| Iodine value | 43.3 | | 80.3 | | 66.7 | |
| m.p. (°C.) | 35.4 | | 33.7 | | 40.9 | |
| Fatty acid composition (%) | total | 2-position | total | 2-position | total | 2-position |
| 16:0 | 1.9 | 1.8 | 2.9 | 0.2 | 6.1 | 1.8 |
| 18:0 | 66.7 | 7.0 | 58.6 | 1.4 | 36.9 | 3.0 |
| 18:1 | 11.6 | 33.7 | 7.3 | 17.6 | 38.6 | 69.4 |
| 18:2 | 18.8 | 56.0 | 8.2 | 19.8 | 17.1 | 23.6 |
| 18:3 | | | 23.0 | 55.6 | | |
| others | 0.7 | 1.6 | | | 1.3 | 2.2 |
| Content of TG having polybasic unsaturated fatty acid group at 2-position (%) | 56 | | 75.4 | | 23.6 | |
| SFC 10° C. | — | | 75.3 | | 68.9 | |
| (%) 20° C. | 83.0 | | 75.0 | | 67.1 | |
| 25° C. | 83.5 | | 69.0 | | 65.0 | |
| 30° C. | 80.4 | | 48.0 | | 57.0 | |
| 33° C. | 69.8 | | 23.0 | | 46.1 | |
| 37° C. | 0.7 | | 0 | | 34.5 | |
| 40° C. | 0 | | — | | 26.1 | |
| 45° C. | — | | — | | 0 | |

What is claimed is:

1. A process for producing a high nutritive value oleaginous composition for confectionary fat or hard butter and combining high solid fat content and high meltability in the mouth which comprises transesterifying a fat containing polybasic unsaturated fatty acid(s) as constituting fatty acid(s) and a saturated fatty acid(s), a saturated fatty acid alcohol ester(s) or mixture thereof, with a lipase having a site-specificity thereby to give an oleaginous composition comprising at least 40% of symmetric triglyercide(s) each having a polybasic unsaturated fatty acid group at the 2-position and at least 50% of completely saturated fatty acid(s) each having 16 or more carbon atoms.

2. A process for producing an oleaginous composition as set forth in claim 1, wherein said polybasic unsaturated fatty acid is linoleic acid.

3. A process for producing an oleaginous composition as set forth in claim 1, wherein said polybasic unsaturated fatty acid is linolenic acid.

4. A process for producing an oleaginous composition as set forth in claim 1, wherein said saturated fatty acid(s) are those having 16 to 18 carbon atoms.

5. A process for producing an oleaginous composition as set forth in claim 1, wherein said saturated fatty acid alcohol ester(s) are those obtained by esterifying a saturated fatty acid having 16 to 18 carbon atoms with a straight-chain saturated monohydric alcohol having one to six carbon atoms.

6. A process for producing an oleaginous composition as set forth in claim 1, wherein said lipase having a site-specificity is a Rhizopus lipase.

7. A process for producing an oleaginous composition as set forth in claim 1, wherein said lipase having a site-specificity is an Aspergillus lipase.

8. The process of claim 7 further comprising mixing corn oil and stearic acid to form said fat.

9. The process of claim 7 further comprising mixing linseed oil and stearic acid to form said fat.

10. The process of claim 1 further comprising mixing corn oil and stearic acid to form said fat.

11. The process of claim 1 further comprising mixing linseed oil and stearic acid to form said fat.

* * * * *